US00PP33924P3

(12) United States Plant Patent
Schoone

(10) Patent No.: US PP33,924 P3
(45) Date of Patent: Feb. 1, 2022

(54) ***PHALAENOPSIS* PLANT NAMED 'PURE LOVE'**

(50) Latin Name: *Phalaenopsis hybrida*
Varietal Denomination: Pure Love

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,974

(22) Filed: Jun. 5, 2021

(65) Prior Publication Data

US 2021/0385998 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Pure Love', characterized by its upright plant habit; moderately vigorous to vigorous growth habit; strong flowering stems; strong leaves; freely flowering habit with typically two inflorescences per plant, each inflorescence with numerous flowers; white-colored flowers that are densely covered with fine purplish pink-colored dots and reddish purple-colored venation with white-colored margin edges; and good postproduction longevity.

2 Drawing Sheets

Figure 1:
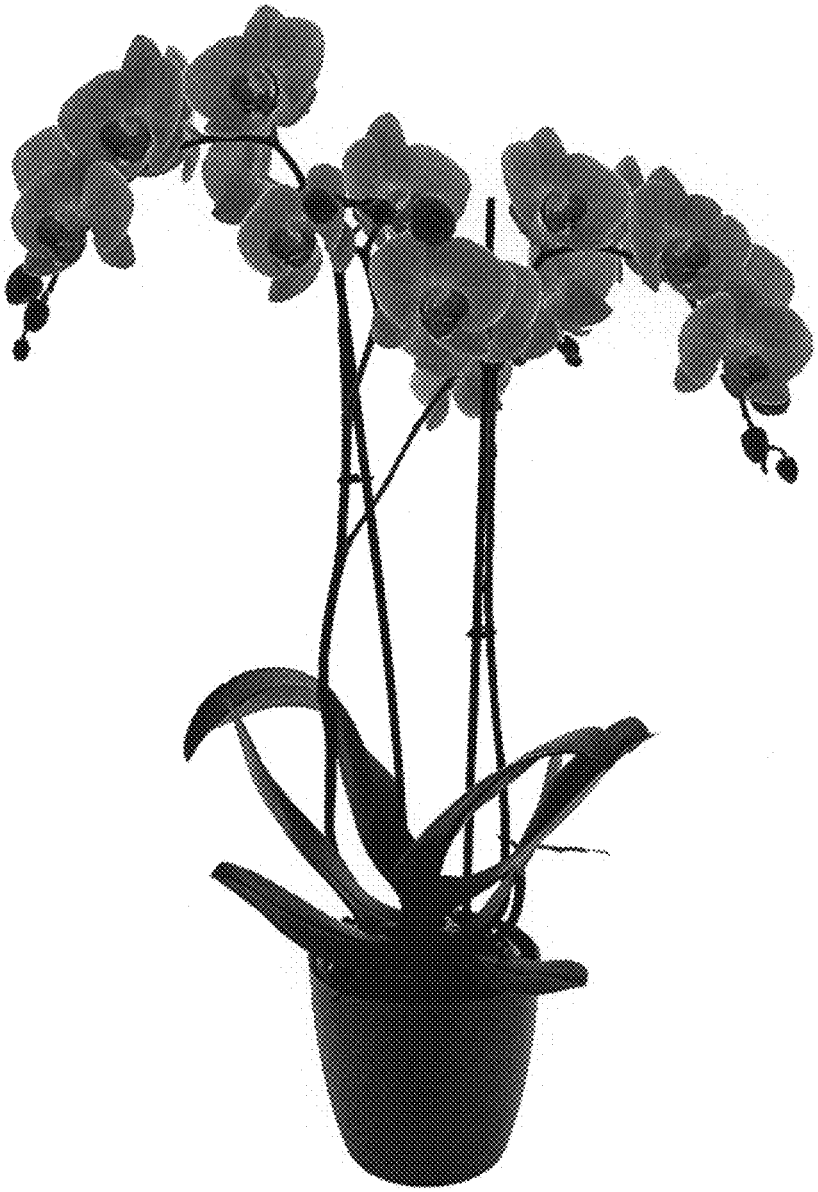

Botanical designation: *Phalaenopsis hybrida.*
Cultivar denomination: 'PURE LOVE'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Sep. 14, 2020, application number 2020/2153. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Pure Love'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in September, 2012 in Nantou, Taiwan of *Phalaenopsis hybrida* 'Modern Rose', not patented, as the female, or seed, parent with a proprietary selection from crossing of *Phalaenopsis hybrida* 'Otohime' X *P. hybrida* 'Cassandra', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in November, 2017.

Asexual reproduction of the new *Phalaenopsis* plant by in vitro meristem propagation in a controlled environment in Assendelft, The Netherlands since November, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Pure Love'. These characteristics in combination distinguish 'Pure Love' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. White-colored flowers that are densely covered with fine purplish pink-colored dots and reddish purple-colored venation with white-colored margin edges.
7. Good postproduction longevity.

Plants of the new *Phalaenopsis* can be compared to plants of the female parent, 'Modern Rose'. Plants of the new *Phalaenopsis* differ primarily from plants of 'Modern Rose' in flower color as flowers of plants of the new *Phalaenopsis* have denser venation than flowers of plants of 'Modern Rose'. In addition, the curvature of the labellum is stronger in plants of the new *Phalaenopsis* than plants of 'Modern Rose'.

Plants of the new *Phalaenopsis* can be compared to plants of the male parent, the proprietary selection from crossing of *Phalaenopsis hybrida* 'Otohime' X *P. hybrida* 'Cassandra'. Plants of the new *Phalaenopsis* differ primarily from plants of the male parent selection in flower color as plants of the new *Phalaenopsis* have white-colored flowers that are densely covered with fine purplish pink-colored dots and reddish purple-colored venation with white-colored margin edges whereas plants of the male parent selection have white-colored flowers with violet-colored venation.

Plants of the new *Phalaenopsis* can be compared to plants of *Phalaenopsis hybrida* 'Harper Seven', disclosed in U.S. Plant Pat. No. 30,682. In side-by-side comparisons, plants of the new *Phalaenopsis* differ primarily from plants of 'Harper Seven' in flower color as plants of the new *Phalaenopsis* have white-colored flowers that are densely covered with fine purplish pink-colored dots and reddish purple-colored venation with white-colored margin edges whereas plants of 'Harper Seven' have purple violet-colored flowers with a central whitish haze. In addition, the curvature of the labellum is slightly weaker in plants of the new *Phalaenopsis* than plants of 'Harper Seven'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Pure Love' grown in a container.

Figure 2:
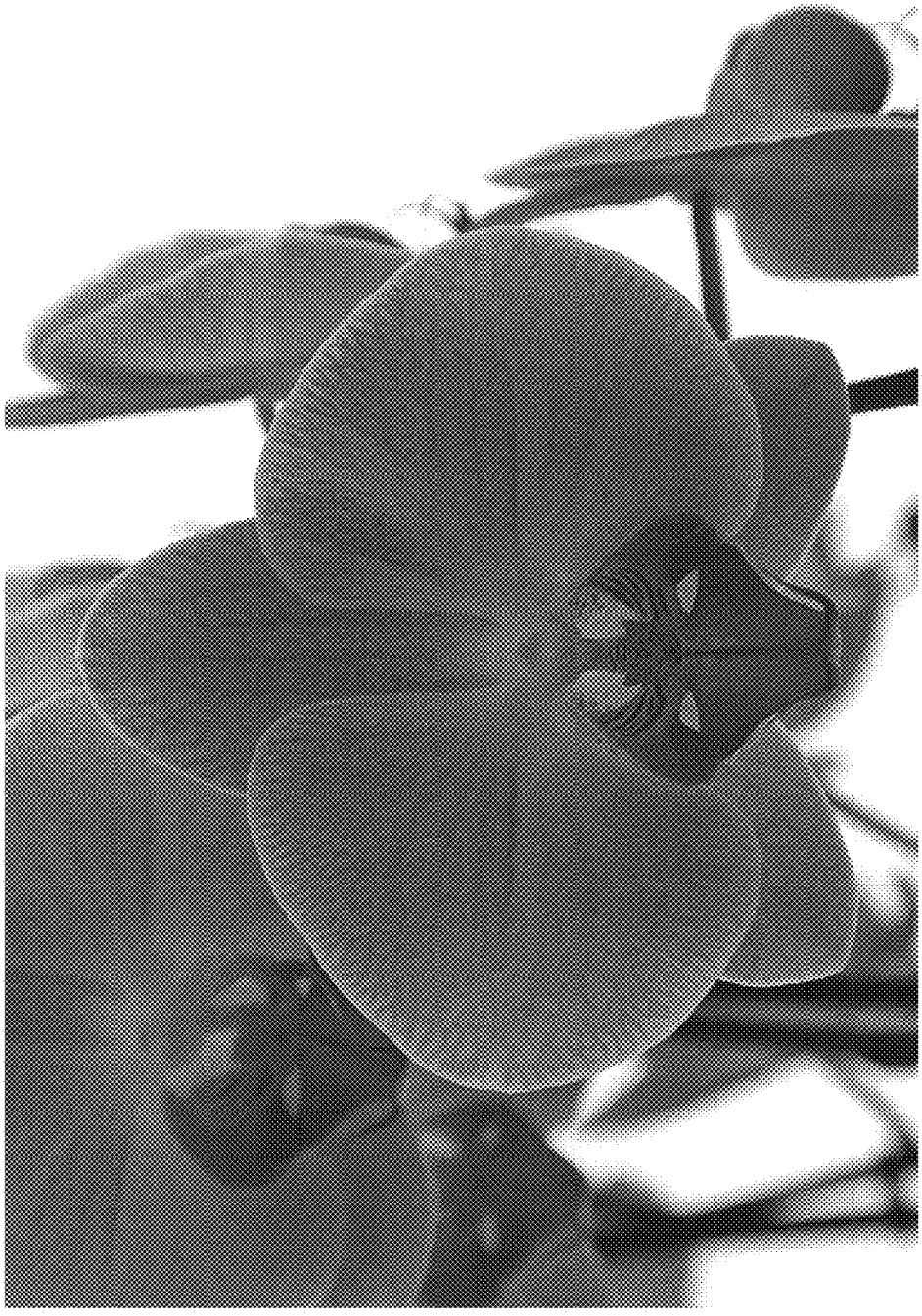

The photograph on the second sheet (FIG. 2) is a close-up view of a typical flower and flower buds of 'Pure Love'.

DETAILED BOTANICAL DESCRIPTION

The aforementioned photographs and following observations and measurements describe plants grown during the early spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Pure Love'.

Parentage:

*Female parent.*—*Phalaenopsis hybrida* 'Modern Rose', not patented.

*Male parent.*—Proprietary selection from crossing of *Phalaenopsis hybrida* 'Otohime' X *P. hybrida* 'Cassandra', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane.*—About 16 cm.

*Plant height, substrate level to top of inflorescences.*—About 50.6 cm.

*Plant diameter or spread.*—About 37.6 cm.

Leaf description:

*Arrangement and quantity.*—Distichous, simple; sessile; about eight leaves per plant.

*Length.*—About 20.2 cm.

*Width.*—About 7.7 cm.

*Aspect.*—Upright to outwardly arching.

*Shape.*—Oblanceolate to elliptic to narrowly elliptic; slightly carinate.

*Apex.*—Unequal acute.

*Base.*—Sheathing. Sheath length: About 1.7 cm. Sheath width: About 1.3 cm. Sheath color: Close to 143C; tinged towards the margins with close to 137C.

*Margin.*—Entire; slightly revolute.

*Texture and luster, upper and lower surfaces.*—Smooth, glabrous; slightly glossy.

*Venation pattern.*—Camptodromous.

*Color.*—Developing leaves, upper surface: Close to NN137A. Developing leaves, lower surface: Close to 146A; margin edges, tinged with close to a blend of N199A and N199B. Fully expanded leaves, upper surface: Close to NN137B; venation, close to NN137B. Fully expanded leaves, lower surface: Close to 146A; margin edges, close to 148A; venation, close to NN137B.

Inflorescence description:

*Appearance and flowering habit.*—Showy zygomorphic flowers arranged on axillary branched racemes; typically two inflorescences per plant; each inflorescence with about 16 to 17 flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about four weeks on the plant; flowers not persistent.

*Inflorescence length (lowermost flower to inflorescence apex).*—About 34.6 cm.

*Inflorescence width.*—About 19.8 cm.

*Flower buds.*—Height: About 1.8 cm. Diameter: About 1.3 cm by 1.5 cm. Shape: Broadly ovate. Color: Close to 183B; towards the base, tinged with close to 146C; venation, close to 183A to slightly darker than 183A.

*Flower size.*—About 7.4 cm (vertical) by 8.4 cm (horizontal).

*Flower depth.*—About 2.9 cm.

*Petals, quantity and arrangement.*—Three, two lateral petals and one center petal transformed into a labellum.

*Lateral petals.*—Length: About 4.1 cm. Width: About 5.1 cm. Shape: Reniform to lunate. Apex: Obtuse. Margin: Entire. Texture and luster, upper and lower surfaces: Smooth, glabrous, velvety; matte. Color: When opening, upper surface: Distal half, close to N75B with dense venation, close to 77B; proximal half, close to 76B with venation, close to N75B; at the base (at column connection), close to 157D. When opening, lower surface: Close to 69A; towards the margins, close to 76B to 76C; at the base, close to 150D; venation, close to 72B. Fully opened, upper surface: Close to N155A; densely covered with fine dots, close to N78C and N78D and venation, close to N78B; at the base (at column connection), close to NN155C; margin edges, close to N155A; color does not change with subsequent development. Fully opened, lower surface: Close to N75C to N75D; venation, close to 77B; color does not change with subsequent development.

*Labella.*—Appearance: Three-parted with two lateral lobes and a central lobe. Length, lateral lobes: About 2 cm. Width, lateral lobes: About 1.6 cm. Length, central lobe: About 3.1 cm. Width, central lobe: About 7 mm to 24 mm. Shape, lateral lobes: Obovate. Shape, central lobe: Deltoid. Apex, lateral lobes: Rounded. Apex, central lobe: Cleft with two narrow and strongly recurved cirrose tips, about 1.4 cm in length and about 2 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 4 mm in length, about 6 mm in width and about 6 mm in height. Color: When opening, upper surface: Lateral lobes: Close to 156D; towards the base, close to 179A and at the base, stripes, close to 183B; dense venation, close to N78B and NN78B. Central lobe: Close to 64C; towards the apex, close to 64B; towards the margins and apex, strongly tinged with close to 175D; at the base (at column connection), close to 157D with radial stripes, close to 185A; main vein, close to 60B; cirrose tips, close to 64C. Callosities: Close to 10A; fine dots, close to 187C. When opening, lower surface: Lateral lobes: Close to 76A to 76B; towards the base, close to 156C; basal margin, close to 166C. Central lobe: Close to 76C; towards the margins and apex, close to 174B; at the base (at column connection), close to 157B; margin edges, close to 61A. Fully opened, upper surface: Lateral lobes: Close to 156D; towards the base, close to 178C to 178D and at the base, tinged with close to 8B and stripes, close to 183B; dense venation, close to N78B and NN78B. Central lobe: Close to 64C; towards the apex, close to 64B; towards the margins and apex, strongly tinged with close to 178C; at the base (at column connection), lighter than 157D with radial stripes, close to 185A; main vein, close to 60B; cirrose tips, close to 64C. Callosities: Close to 13B; fine dots, close to 187C. Fully opened, lower surface: Lateral lobes: Close to 76A; towards the base, close to 156D; basal margin, close to 166C. Central lobe: Close to N75D; towards the margins and apex, close to 174B; at the base (at column connection), close to 157B; margin edges, close to 61A.

*Sepals.*—Quantity and arrangement: Three, one upper dorsal sepal and two lower lateral sepals. Length, dorsal sepal: About 4.5 cm. Width, dorsal sepal: About 3 cm. Length, lateral sepals: About 4.3 cm. Width, lateral sepals: About 2.9 cm. Shape, dorsal sepal: Elliptic to ovate. Shape, lateral sepals: Ovate. Apex, dorsal sepal: Bluntly acute. Apex, lateral sepals: Narrowly obtuse to bluntly acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to 76B and 76C; fine dots, close to N75B and N75C; venation, close to N78B. When opening, lower surface: Close to 184D; towards the margins and apex, close to N74C; venation, close to 184A to 184B. Fully opened, upper surface: Close to N155C; densely covered with fine dots, close to N78C and N78D and venation, close to N78B; at the base (at column connection), close to NN155C; margin edges, close to N155A. Fully opened, lower surface: Close to N78C; towards the margins, close to N80C to N80D; venation, close to NN78B. Color, lateral sepals: When opening, upper surface: Distally, close to 157D and tinged with close to N75A with venation, close to 77B; proximally, close to 157D and at the base, close to 154D with blotches and fine dots, close to 184A. When opening, lower surface: Close to 185C fading to closer to 152D; venation, close to 183C. Fully opened, upper surface: Close to N155C; densely covered with fine dots, close to N78C and N78D and venation, close to N78B; at the base (at column connection), close to 155C with blotches and fine dots, close to 72C; margin edges, close to 76C to 76D. Fully opened, lower surface: Close to N78C; towards the apex, close to N78B; at the base, close to 157B; venation, close to 71B.

*Peduncles.*—Length: About 61 cm. Diameter: About 6 mm. Strength: Strong. Aspect: Upright to outwardly arching. Texture and luster: Smooth, glabrous; matte. Color: Close to 138A to 138B; densely covered with fine dots, close to 147A; proximally, dots becoming denser and closer to N189A.

*Pedicels.*—Length: About 3.5 cm. Diameter: About 3 mm. Strength: Moderately strong. Aspect: About 50° from peduncle axis. Texture and luster: Smooth, glabrous; matte. Color: Close to 146C; proximally, close 147A and distally, close to 157A and tinged with close to 75B.

*Reproductive organs.*—Androecium: Column length: About 8 mm. Column width: About 6 mm. Column color: Close to N75D to lighter than N75D. Pollinia quantity: Two. Pollinia diameter (per two pollinia): About 2.5 mm. Pollinia color: Close to 23A. Gynoecium: Stigma length: About 3 mm. Stigma width: About 4.5 mm. Stigma shape: Reniform. Stigma color: Close to N155A. Ovary length: About 6 mm. Ovary diameter: About 1 mm. Ovary color: Close to 150A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Pure Love' as illustrated and described.

* * * * *